United States Patent
Tayot

(10) Patent No.: US 6,949,625 B2
(45) Date of Patent: Sep. 27, 2005

(54) INJECTABLE IMPLANT OF INSOLUBLE GLOBIN

(75) Inventor: Jean-Louis Tayot, La Tour de Salvagny (FR)

(73) Assignee: Khorionyx, La Tour de Salvagny (FR)

( * ) Notice: Subject to any disclaimer, the term of this patent is extended or adjusted under 35 U.S.C. 154(b) by 0 days.

(21) Appl. No.: 10/842,462

(22) Filed: May 11, 2004

(65) Prior Publication Data

US 2004/0248774 A1 Dec. 9, 2004

Related U.S. Application Data

(60) Provisional application No. 60/472,467, filed on May 22, 2003.

(30) Foreign Application Priority Data

May 12, 2003 (FR) ............................................ 03 05700

(51) Int. Cl.[7] .......................... A61K 35/14; A61K 47/00
(52) U.S. Cl. ........................ 530/385; 530/356; 514/773
(58) Field of Search ................................ 530/356, 385; 514/773

(56) References Cited

U.S. PATENT DOCUMENTS

| 2,161,198 A | 6/1939 | Reiner |
| 2,460,550 A | 2/1949 | Strumia et al. |
| 4,518,525 A | 5/1985 | Autio et al. |
| 4,543,209 A | 9/1985 | Tayot et al. |
| 2002/0122816 A1 | 9/2002 | Sung et al. |

FOREIGN PATENT DOCUMENTS

| GB | 494327 | 10/1938 |
| WO | WO 98/19718 | 5/1998 |
| WO | WO 99/17786 | 4/1999 |

OTHER PUBLICATIONS

He et al., "Expression, purification, and characterization of human hemoglobins Gower–1, Gower–2, and Portland–2 assembled in complex transgenic–knockout mice", 2001, Blood, 97(4), 1099–1105.*

Reiner, "Globin zinc insulin", Canadian Medical Association Journal, Feb. 21, 1976, vol. 114, pp. 293–294.

Teale, "Cleavage of the haem–protein link by acid methylethylketone", Biochem. Biophys. Acta (1959), vol. 35, p. 543.

Anson et al., "Protein Coagulation and Its Reversal", J. Gen. Physiol., 13, 1930, pp. 469–476.

Autio et al., "Chemical and Functional Properties of Blood Globin Prepared by a New Method", Journal of Food Science, vol. 49, 1984, pp. 859–862.

Autio et al., "Penetration Studies of Blood Globin Gels", Journal of Food Science, vol. 50, 1985, pp. 615–617.

Beardwood et al., "Comparison of Diabetic Control with NPH and Globin Insulin", Journal of the Michigan State Medical Society, 1952, 51, 10, pp. 1298–1302.

Berg et al., "Comparison of Globin Insulin and NPH Insulin", Diabetes, vol. 2, No. 5, Sep.–Oct. 1953, pp. 365–369.

Kriegler et al., "Identification of the 'Factor' in Erythrocyte Lysates Which Enhances Colony Growth in Agar Cultures", Exp. Hematol., Jan. 1981, vol. 9, No. 1, pp. 11–21.

Liepke et al., "Human hemoglobin–derived peptides exhibit antimicrobial activity: a class of host defense peptides", J. Chromatogr., 791, 2003, pp. 345–356.

Rabinowitch et al., "Globin Insulin", The Canadian Medical Association Journal, vol. 56, No. 6, Jun. 1947, pp. 595–605.

Reiner et al., "Insulin Preparations with Prolonged Activity, I. Globin Insulin", Proc. Soc. Exp. Biol. Med. (1939), No. 40, p. 171.

Rossi–Fanelli et al., "Pure native globin from human hemoglobin: preparation and some physico–chemical properties", Biochem. Biophys. Acta., vol. 28, 1958, p. 221.

Rossi–Fanelli et al., "Studies on the Structure of Hemoglobin I. Physicochemical Properties of Human Globin", Biochem. Et Biophys. Acta., vol. 30, 1958, pp. 608–615.

Schulz, "Der Eiweisskorper des Hamoglobins", Ztsdr. J. Physiol. Chem., vol. 24, 1898, pp. 449–481.

Strumia et al., "The use of a 'modified globin' from human erythrocytes in hypoproteinemias", Am. J. M. Sci., vol. 211, 1946, pp. 51–61.

Strumia et al., "The use of a 'modified globin' from human erythrocytes as a plasma substitute", Am. J.M. Sci., vol. 203, 1945, pp. 436–442.

Strumia et al., "Modified Globin", The Journal of Laboratory and Clinical Medicine, vol. 40, No. 2, 1952, pp. 211–222.

Strumia et al., "Modified Globin", The Journal of Laboratory and Clinical Medicine, vol. 37, No. 6, 1951, pp. 359–368.

Tybor et al., "Effect of decolorization and lactose incorporation on the emulsification capacity of spray–dried blood protein concentrates", Journal of Food Science, vol. 38, 1973, pp. 4–6.

Vars et al., "Modified Globin", The Journal of Laboratory and Clinical Medicine, vol. 39, No. 5, 1952, pp. 743–751.

* cited by examiner

Primary Examiner—Robert A. Wax
Assistant Examiner—Suzanne M. Mayer
(74) Attorney, Agent, or Firm—Stites & Harbison PLLC; B. Aaron Schulman

(57) ABSTRACT

A preparation is provided which can be injected or implanted into the human or animal body, and which comprises, as main component, globin that is insoluble at physiological pH, biocompatible and sterile.

56 Claims, No Drawings

INJECTABLE IMPLANT OF INSOLUBLE GLOBIN

CROSS-REFERENCE TO RELATED APPLICATIONS

This application claims benefit of U.S. Provisional Application No. 60/472,467, filed May 22, 2003, incorporated herein by reference.

FIELD OF THE INVENTION

The aim of the present invention is to provide globin preparations that are useful for administration to humans. These preparations may in particular be in the form of injectable pastes or of implantable solid materials, or of implants.

BACKGROUND OF THE INVENTION

Many medical applications of collagen have already been described, whether in the form of pastes, for example for filling, of fluid or solid formulations, such as films or compresses, or in the form of diverse implants. In fact, only animal collagen is generally used.

The preparation of human collagen, which would be preferable to animal collagen, can be envisioned from human cutaneous tissues. However, it is made very difficult since the taking of human tissue samples from cadavers poses considerable ethical problems and requires expensive tests in order to eliminate the risks of transmission of infectious diseases, viral diseases or the like. The preparation of human collagen from placentas is expensive, complex and difficult to organize. The preparation of human collagen by the modern methods of genetic recombination or of cell culture is also very expensive, which would certainly impair the commercial development of this product.

Globin is the protein constituting hemoglobin, which, itself, contains 4 peptide chains (2 α-chains and 2 β-chains), each associated with a heme. The heme consists of a tetrapyrole structure containing one positively charged iron atom. There are 4 hemes per molecule, responsible for the red coloration of hemoglobin.

The processes for preparing globin have been known for a very long time and have been developed with dietary application being the aim, or for preparing injectable pharmaceutical solutions.

Unlike hemoglobin, which is completely soluble at physiological pH, globin is notably insoluble under the same conditions. The insoluble nature of globin under physiological conditions has, to date, impaired the development of its pharmaceutical applications. For this reason, most experiments have sought to prepare globin derivatives which are soluble at physiological pH, in particular by succinylation using succinic anhydride or by acetylation using acetic anhydride, or by hydrolysis of the amide functions at alkaline pH, which increases the negative charge of globin and decreases its isoelectric pH. An injectable product combining a soluble preparation of acid globin with insulin has been developed, patented and marketed: Reiner (1939); Reiner et al. (1939). It allows, after injection, gradual delivery of the insulin from this complex: Rabinowitch et al. (1947); Berg et al. (1953). Globin is not the active element or the main element of this product.

SUMMARY OF THE PRESENT INVENTION

The present invention proposes to provide novel materials and injectable preparations or preparations which are implantable in the organism, in which the globin is the main active element, and which do not have the drawbacks of the known materials and formulations, for example of collagen or the like.

A subject of the invention is a pasty or solid preparation of globin that is insoluble at physiological pH, biocompatible, sterile and, preferably, biodegradable, in particular in the form of an injectable paste, of solid materials, for example of granules or of films, or of insoluble implants.

DETAILED DESCRIPTION OF THE INVENTION

The present invention proposes to conserve the natural insoluble nature of globin at neutral pH, for example by harvesting, by centrifugation, a protein precipitate of globin formed by suspension of this precipitate in a pharmaceutically acceptable vehicle, for example an aqueous physiological solution of PBS type, containing 9 g/l NaCl and buffered at neutral pH between 6.8 and 7.5. The paste thus formed is injectable after homogenization using a fine needle. This paste can be prepared in the presence of viscous agents and lubricants such as solutions of triglycerides, of polyethylene glycol, of hyaluronate, in particular sodium hyaluronate, of hyaluronic acid or of other polysaccharides or mucopolysaccharides or of oxidized cellulose. Such an additive facilitates passage of the pasty precipitate to the finest needles (diameter 30 g) and injection thereof as intradermal implant.

The originality and the advantage of this product lie in the fact that it is a protein paste that is completely biocompatible with the surrounding tissues into which it is injected. This protein has undergone no alteration or chemical modification, it is naturally insoluble from the moment it is in a physiological environment. A protein paste of human globin can be used in humans for filling skin cavities, wrinkles or scars, or augmenting the volume of certain tissues (urinary or digestive sphincters, vocal chords, etc.). This paste can be used to fill bone or cartilage defects and to facilitate the cicatrization thereof. Particles of insoluble globin can also be used in animal or human cell culture. The cells, which have a negative electric charge, attach to the surface of the positively charged globin particles and multiply at their surface. Gradual degradation of the globin support, in contact with the cells which gradually digest it, can in addition provide a means of nutrition for the cells which supplements or is an alternative to the liquid culture media used to date.

The filling applications permitted by this globin paste are therefore numerous and unexpected for this protein.

The homologous human globin is preferable and makes it possible to avoid any immunological reaction by the patient to be treated, during or after injection. This product therefore represents a considerable advantage with respect to the collagen which to date is prepared from animal skin (calf, pig, etc.) and which requires a certain number of precautions and conditions in order to avoid immunological reactions in the patients.

Need to test each patient for a possible allergy to the animal collagen.

Impossibility of treating allergic individuals.

The globin remains, however, soluble at acidic or basic pHs and, under these conditions, can be sterilely filtered through porous membranes. For suitable concentrations of 20 to 300 mg/ml, such solutions can be treated like protein solutions and make it possible to prepare products such as:

sponges, films or granules, using or combining the techniques of drying, lyophilization, crosslinking and precipitation. Some examples are developed below.

Globin is easy to purify from red blood cells originating from animal or human blood. Human red blood cells are available in sufficient amount from donations which have passed their shelf-life, remaining in stock in blood transfusion centers and for which all the prior health tests were carried out at the time the sample was taken. The preparation of insoluble, injectable globin or of other globin-based biomaterials therefore represents novel biomedical applications making it possible to recover unused blood or blood donations which have passed their shelf-life, and to avoid or decrease their destruction.

The invention can also be implemented using a blood sample, of approximately 5 to 100 ml, taken from the patient to be treated, and converting it into autologous globin with the same methods as for large volumes, and then injecting the paste obtained, for the correction of wrinkles in the same patient or other applications such as chronic wound healing. The number of syringes prepared using a sample from the patient may be considerable and may allow the patient to be treated for several years.

Similarly, human placenta, which is delivered after the birth, contains blood which is generally destroyed by incineration, but which can also be used for the invention.

Bags of blood from donors are officially controlled by the blood transfusion organizations, by virtue of biochemical, bacteriological and serological examinations and screening tests for the various viruses and other infectious agents. In the case of placental blood, it would obviously be necessary to carry out the same examinations on blood samples from the umbilical cord or from the mother, before being able to collect, conserve and extract the blood from this starting material. For the autologous blood, the tests to be carried out can be simplified.

The implementation of the invention first requires the harvesting and purifying of the red blood cells in these blood samples, or blood fluids, by simple operations which are already known. The red blood cells are recovered by low-speed centrifugation. The plasma supernatant is separated and replaced with a physiological saline liquid of PBS type, containing 9 g/l of NaCl and buffered at neutral pH.

After several washes (3 to 5), the plasma proteins are thus removed from the red blood cell suspension. One or two volume(s) of distilled water is (are) added to the pellet of purified red blood cells in order to perform an osmotic shock which results in lysis of the blood cell membranes and releases the hemoglobin in solution, concentrated and purified. A high-speed centrifugation step (10 to 20 000 rpm) makes it possible to remove the membrane and cell debris in the pellet. A final step consisting in filtration of the supernatant through a membrane with a porosity of 0.2 micron makes it possible to prepare a purified and sterile hemoglobin solution free of particles and derivatives of tissue, cell or membrane origin.

Heme-globin cleavage at acid pH was described in the presence of alcohol by Schulz as early as 1898. Anson and Mirsky in 1930, and then Rossi-Fanelli et al., in 1958, used acetone in the presence of acid at 0° C. Teale (1957) preferred the use of methyl ethyl ketone in place of the acetone. Autio et al. (1984) separated the globin at acid pH by virtue of absorption and precipitation of the heme with soluble carboxymethylcellulose. The globin thus prepared is soluble at acid or alkaline pH, but becomes insoluble as soon as the pH of the aqueous solution is neutralized to between pH 6 and 8.

Solubilization experiments at neutral pH were carried out by Strumia et al., in 1951 and 1952, using a prolonged alkaline treatment which results in partial deamidation of the globin at the asparagine and glutamine residues, converted respectively to aspartic acid and glutamic acid (Vars, 1952). Other solubilization experiments were carried out by Volckmann in 1988, by succinylation.

The insoluble nature in physiological medium explains the persistence of the globin after tissue implantation, which also makes it resistant to enzymatic degradation, especially if the amount injected is considerable, which is the case in filling or tissue augmentation applications.

On the other hand, most other proteins can only be precipitated by high concentrations of salts or of alcohol, which will make their precipitates non-biocompatible and non-usable for intra-tissue injections. In addition, such implants will disappear very rapidly by diffusion of the precipitating agents and gradual dissolving of the precipitate on contact with the physiological medium of the tissues.

The advantage of the invention can be readily verified using a preparation of rabbit globin. The physiological, precipitated globin paste thus prepared can be injected subcutaneously at various places on the back or the side of the rabbit. It is easy to verify the innocuity by the absence of local erythema. The persistence of the product under the skin can be observed by palpation as a function of time. The absence of antigenic capacity of the product can be verified by a subcutaneous and intramuscular immunization of rabbits, with or without Freund's adjuvant. Blood samples taken after the immunization make it possible to verify the absence of anti-globin or anti-hemoglobin antibodies using the conventional control tests.

EXAMPLES OF PRODUCTION OF PRODUCTS ACCORDING TO THE INVENTION

Example 1

Preparation of Rabbit Globin

Five anesthetized rabbits are bled by cardiac puncture. The blood is recovered in the presence of heparin or in the presence of sodium citrate so as to avoid clotting thereof. 210 ml of blood are thus obtained, which are centrifuged for 30 minutes at 2500 rpm. The supernatant containing the plasma is removed with a pipette and the pellet is washed 5 times with 3 volumes of PBS buffer, containing 9 g/l NaCl and buffered at pH 7.2. An equal volume of distilled water is added, with stirring, to the washed final pellet in order to lyse the red blood cells. The final suspension is centrifuged at 12 000 rpm in order to remove cell and membrane debris. The supernatant is filtered through a cellulose acetate membrane with a porosity of 0.22 micron. 82 ml containing 97 g/l of hemoglobin are obtained.

The hemoglobin is converted into globin according to the technique described by Tayot and Veron (1983). This hemoglobin solution is poured, with stirring, into 275 ml of 96% ethanol containing 1 ml of concentrated HCl. The pH is adjusted to 3. The final concentration is 74% of ethanol and 22 g/l of hemoglobin at acid pH. 3 g of CECA L4S active charcoal are added with vigorous stirring for 15 minutes at 4° C.

The suspension is centrifuged at 15 000 rpm for 30 minutes in order to remove the charcoal in the form of a pellet. The supernatant containing the decolorized acid globin is filtered through a series of porous membranes, to the smallest porosity (0.2 micron), in order to remove the fine particles of charcoal. The filtrate is diluted with an equal volume of distilled water, the pH is adjusted to 7.4 by addition of NaOH, and the globin precipitates en masse. After 15 hours, the globin precipitate is recovered by centrifugation, and then washed twice with 3 volumes of PBS physiological saline containing 9 g/l NaCl and buffered to pH 7.4. 58.2 g of globin precipitate are harvested at pH 7.4. The precipitate is homogenized by successive transferring between two syringes with a volume of 5 ml, linked via a connector with an inner diameter of 1 to 0.2 mm, by successively pushing the plunger of each syringe so as to cause the precipitate to pass into the other syringe.

Finally, the homogenized precipitate is distributed into 1 ml syringes. It is possible to expel the precipitated globin paste from the syringe, through fine needles of diameter 24 or 27 g. The concentration of globin in the paste can be adjusted to values of between 30 and 150 mg/g.

Example 2

Preparation of Human Globin 200 ml of human blood which has passed its shelf-life, taken on sodium citrate, are centrifuged for 30 min at 2500 rpm. The supernatant containing the plasma is removed with a pipette, also taking up by suction the superficial whitish cell layer corresponding to the leukocytes. The pellet of red blood cells is washed 5 times with 3 volumes of PBS physiological saline containing 9 g/l NaCl and buffered at pH 7.2, by successive centrifugations. 2 volumes of distilled water are added to the final pellet in order to lyse the red blood cells. The hemolyzed suspension is clarified by centrifugation for 30 min at 12 000 rpm and filtered through a membrane with a porosity of 0.2 micron. 210 ml containing 52 g/l of hemoglobin are obtained, which are conserved at 4° C.

An equal volume of 210 ml of 0.1 N HCl at 4° C. is added, and the entire mixture is poured into 4 l of acetone containing 40 ml of 1 N HCl. The suspension is stirred vigorously and left to stand for one hour at ambient temperature, under a chemical hood. The heme dissolved in the acetone is removed by filtration through porous cloth and the globin precipitate is recovered, washed in acidic acetone and dried under a stream of air.

In a variant, various inorganic acids (sulfuric acid, phosphoric acid, etc.) or carboxylic acids, such as acetic acid, oxalic acid or citric acid, for example, can be used in place of the hydrochloric acid in order to acidify the hemoglobin solution before its decoloration.

Another variant of this process consists in precipitating the acid solution of hemoglobin before decolorizing it. The precipitation can be carried out by adding NaCl at a concentration of 40 to 60 g/l. The acid hemoglobin precipitate is then decolorized by suspension in a sufficient volume of ethanol and/or of acetone. The pigment dissolves in the ethanol and/or the acetone; the globin remains in precipitated form and can be harvested by filtration through porous cloth. By virtue of the elimination of any aqueous phase, this variant makes it possible to reduce the required volume of ethanol and/or of acetone by a factor at least equal to 5.

The globin is redissolved in aqueous solution at a pH between 2 and 3. The aqueous acid globin solution is filtered sterilely through a membrane with a porosity of 0.2 micron, and then precipitated by neutralization of the pH by adding NaOH until a pH of 7.4 is obtained. Syringes of globin paste precipitated at neutral pH can be prepared as in the preceding example. The operation to neutralize the acidic globin solution can be carried out by adding sodium hyaluronate at alkaline pH. In this case, there is formation of a paste of insoluble globin complexed and impregnated with the hyaluronate, providing a lubricating function which improves the injectable nature through very fine needles (diameter 30 g).

Example 3

Other Preparation of Human Globin

The process of Example 1 is carried out using a controlled blood cell pellet which has passed its shelf-life, obtained from a blood transfusion center. Syringes containing a paste of precipitated human globin which is biocompatible and implantable by injection are obtained.

Example 4

Preparation of Human Globin having Undergone Alkaline Treatment With 0.1 or 1 M Sodium Hydroxide for 1 Hour at 20° C.

The process of Example 1 or 2 is carried out until the globin precipitate is obtained at pH 7.4, before washes. This precipitate is dissolved, again, in 3 volumes of 0.1 M to 1 M NaOH at 20° C. for one hour, with stirring.

The solution is then neutralized by the addition of an equal volume of HCl of the same molarity and the pH of the suspension is adjusted between and 7 and 7.4. The globin precipitate is then harvested by centrifugation and then washed in PBS physiological saline as in the preceding examples. The precipitated globin paste, to which hyaluronic acid, or other biocompatible viscous and lubricating products: triglycerides, polyethylene glycol, oxidized cellulose, chitosan, etc., may have been added, is distributed into syringes and the injectable nature of the product obtained through very fine needles for intradermal use is again verified. This alkaline treatment of the globin makes it possible to improve the health safety guarantees for the product without significantly modifying the insoluble nature of the globin at neutral pH.

Example 5

Preparation of a Paste of Precipitated and Glutaraldehyde-crosslinked Globin

This treatment is possible in order to increase the implant resorption time. The final globin precipitate is suspended at 2% in PBS. Glutaraldehyde is added, with stirring, at a concentration of 1 mg/g of precipitate. After incubation for 1 hour at 20° C., the globin precipitate is washed and placed in syringes as in the preceding examples.

Other crosslinking agents such as dialdehydes or polyaldehydes can be used, in particular polysaccharides oxidized with periodic acid, such as oxidized dextran, oxidized starch, or oxidized hyaluronic acid.

Example 6

Preparation of Syringes of Sterile Precipitated Globin Paste

To prepare sterile syringes, it is necessary to work under aseptic conditions as soon as sterilizing filtration of the acidic globin solution through a membrane with a porosity of 0.2 micron has taken place. This can be done under a laminar flow hood in a class 100 or 1000 sterile zone, or with a sterile chamber, accessible from the outside via flexible latex gloves. The operations of precipitation, separation by settling out, or centrifugation of the precipitate should be performed in sterile containers wrapped in a protective film.

Another method consists in distributing an acidic solution of soluble globin, which has been sterilely filtered, into a first syringe and a second alkaline solution, which has been sterilely filtered, into a second syringe. The pH of each syringe is adjusted in such a way that the subsequent mixture thereof is at neutral pH. The linking of these two syringes, by virtue of a sterile connector, makes it possible to produce a sterile homogeneous mixture of neutral pH, via successive transfers from one syringe to the other. A sterile precipitate is obtained by spontaneous precipitation of the globin. The suspension obtained can be concentrated by extrusion through fine needles which only allow the aqueous phase to pass. The optional addition of sodium hyaluronate or of any other viscous and lubricating agent to the syringe of concentrated globin makes it possible to incorporate it into the final globin. In a variant, it is possible to also incorporate a crosslinking agent, at the time the two initial syringes are mixed, in order to extend the in vivo resorption time of the globin.

Example 7

Final Sterilization of the Syringes of Precipitated Globin Paste

A sterilization of the syringes prepared according to any one of the preceding examples can be carried out by irradiation at a dose of between 5 and 30 kilogray. The various globin preparations are insoluble before and after sterilization thereof by irradiation. In both cases, the globin insoluble at neutral pH becomes soluble if acidification to pH 3 is carried out with any acidic aqueous solution.

Example 8

Production of an Insoluble Gel or Film from Unmodified Soluble Globin

A solution of soluble globin is prepared by dissolving the acetone-based globin powder at pH 3, at a concentration of 20 to 120 mg/ml, in aqueous solution. This solution is sterilely filtered through a membrane with a porosity of 0.2 $\mu$, and then adjusted to pH 5 by adding sterile 1 N NaOH with stirring.

Oxidized starch at pH 3.5, or another aldehyde, or crosslinking polyaldehyde, containing at least 5 carbon atoms per molecule, is added to the mixture at a concentration of 0.5% with stirring for 5 min. The sterile mixture is poured over a flat surface in order to obtain a thickness of 1 to 3 mm of liquid, at a temperature of 20 to 37° C., under a laminar flow.

The liquid product gradually gels by virtue of the crosslinking of the globin chains, induced by the oxidized starch, and then dehydrates under the stream of air, if it is desired to obtain a film.

The final film, at a thickness of between 20 and 200 $\mu$, according to the initial concentration of material, can be sterilized by beta- or gamma-irradiation or with ethylene oxide. Well-known film-forming agents can be added, such as collagen, gelatin, hyaluronic acid, oxidized cellulose or other polysaccharides or mucopolysaccharides, polyethylene glycol, glycerol, etc. Such an additive makes it possible to give the film flexibility and/or strength. Such a film can be used alone to protect a cutaneous or surgical wound, or to promote healing, or can be associated with various prostheses (vascular prostheses, strengthening lattices, porous matrices) in order to make them impermeable, or to improve their biocompatibility, or confer anti-adhesion properties of an adhesive nature, or to accelerate cell colonization of these prostheses, according to known techniques already used with other products.

In a variant, it is possible to produce a film from globin soluble at pH 5 as previously, but without introducing any crosslinking agent. The final crosslinking of the dried film is performed by the final irradiation which creates covalent bonds between the globin chains. Such a film can then be bonded to the tissues using biologically compatible adhesives reactive with the amino groups of the globin. Preferably, the polyaldehydes obtained by periodic oxidation of polysaccharides can be used. By way of example, oxidized dextran or oxidized starch are preferred.

Example 9

Biomedical Applications of the Insoluble Globin Particles as a Cell Culture Support The sterile paste of globin precipitate at neutral pH obtained in any one of the preceding examples is incubated, for example, with DMEM medium for cell cultures, at a temperature in the region of 37° C. A suspension is obtained, into which the cells are introduced at a density of 10 000 to 100 000 cells/ml. After stirring for 30 minutes and separation by settling out for 1 hour to 15 hours, the cells attach to the globin particles and multiply at their surface for the duration of the culture, which can be from 3 to 12 days. The cell culture medium is chosen as a function of the cell type according to currently published knowledge.

At the end of multiplication, the cell suspension attached to the globin particles can be concentrated by spontaneous separation by settling out. The cell paste obtained can be placed in syringes and injected as a biocompatible cell-containing implant for various therapeutic applications known at this time.

The culturing of skin fibroblasts, according to this method, can allow the preparation of cell-containing implants for skin healing applications or connective tissue filling applications.

The culturing of chondrocytes, according to this method, can allow the preparation of cell-containing implants for applications consisting in filling and healing superficial cartilage injuries.

The culturing of osteoblasts, according to this method, can allow the preparation of cell-containing implants for applications consisting in filling and healing bone fractures or bone losses.

Similarly, stem cells, in particular of embryonic origin, or from umbilical cord blood or from bone marrow, or isolated from various adult tissues, can be cultured on these globin particles and can perform the desired functions after injection or implantation of the cell-containing paste.

For biomedical applications such as the production of viruses or of the derived vaccines, in which the cells can be separated, after culturing, from their globin support, conventional trypsinization methods can be used. The nondegraded globin particles settle out spontaneously at the bottom of the flask and can be separated from the cells by settling out.

In certain variants, it is possible to replace the globin particles with films containing the insoluble globin. The cell culturing can then be carried out by continuous circulation of the culture medium in contact with these flat films, as for any cell cultures on membranes or films known today. This method makes it possible to also produce cell-containing films which can be implanted for specific medical applications.

Example 10

Medical Applications of the Implants of Injectable Insoluble Globin

The preparations according to the invention, and in particular the syringes of insoluble globin prepared according to any one of examples 1 to 7, can be used in the following nonlimiting applications:

Filling of wrinkles and defects in the skin.

Filling of connective tissues or sphincters for applications in urology: vesicoureteral reflux in children, female stress incontinence; in ENT: correction of vocal cord volume.

Hemostatic plug for percutaneous arterial wounds.

Skin cicatrization, using the globin paste alone or in combination with other healing products or growth factors.

Cartilage or bone cicattization, using the globin alone or in combination with other healing products: calcium phosphate, calcium carbonate, hydroxyapatite, growth factors of BMP type.

Combination with antibiotics in order to inhibit bacterial development during the period of colonization and degradation of the implant.

A subject of the invention is also the processes for treating the human or animal body, comprising at least one step of administration of a therapeutically effective amount of an injectable or implantable preparation according to the invention to a patient who exhibits a need for such preparation.

These processes comprise in particular administrations corresponding to the abovementioned applications, performed parenterally or surgically by injection or implantation, or cutaneously.

Bibliography

ANSON M. L. - MIRSKY A. E. (1930)
Protein Coagulation and its reversal. The preparation of insoluble globin, soluble globin and heme.
J. Gen. Physiol. 13, 469–476
AUTIO X - KIESVAARA M. - MALKKI Y. - KANKU S. (1984)
Chemical and functional properties of blood globin prepared by a new method
Journal of Food Science 49, 859–862
BERG J. W. - ORTMEYER D. W. - OTT D. L. - JACKSON R. L. (1953)
Comparison of Globin Insulin and NPH Insulin Diabetes, 2, 5, p. 365–369
RABRNOWITCH I. M. - FOWLER A. F. - BENSLEY E. H. - GORDON A. L. - MOUNTFORD M. (1947)
Globin Insulin
The Canadian Medical Association J., 56, 6, p. 595–605
REINER L. (1939)
Insulin preparation
U.S. Pat. No. # 2,161,198
REINER L. - SEARLE D. S. - LANG E. H. (1939)
Insulin preparations with prolonged activity
I. Globin Insulin
Proc. Soc. Exp. Biol. Med. 40, p. 71
ROSSI-FANELLI A. - ANTONINI E. - CAPUTO A. (1958)
Studies on the structure of haemoglobin
I-Physicochemical properties of human globin
Biochem. Biophys. Acta 30, 608–615
SCHULZ F. N. (1898)
Der Eiweisskböper des hemoglobins [The protein body of hemoglobin]
Ztsch. F. physiol. Chem. 24, 449–460
STRUMIA M. M. - SAMPLE A. B. - MMWR B. (1951)
Modified globin
I-Method for preparation from human erythrocytes.
J. Lab. and Clin. Med. 37, 959–968
STRUMIA M. M. - McGRAW J. J. - SAMPLE A. B. - WR B. (1952)
Modifed globin
IV- Some of the physiological properties of modified human globin
J. Lab. and Clin. Med. 40, 2, 211–222
TAYOT J. L. - VERON J. L. (1983)
Brevet Institut Mérieux [Mérieux Patent Institute]: FR 8311324
Process for preparing globin from haemoglobin and globin obtained by this process.
U.S. Pat. No. 4,543,209 (1985)
TEALE F. W. J. (1957)
Cleavage of the haem-protein link by acid methyl-ethyl keton
Biochem. Biophys. Acta 26, 437
VARS H. M. - BOXER G. E. - MAWR B. (1952)
Modified Globin
II- Chemical changes in human globin by alkaline modification
J. Lab. and Clin. Med. 39, 5, 743–751
VOLCKNN H. (1988)
Essais de développement d'un substitut plasmatique d'origine placentaire [Attempts to develop a plasma substitute of placental origin]
Thèse d'ngénieur [Engineer's thesis] CNAM—Lyon

What is claimed is:

1. A preparation that can be injected or implanted into the human or animal body, which comprises, as main active component, globin that is insoluble at physiological pH, biocompatible and sterile, in the form of an injectable homogenous paste.

2. The preparation as claimed in claim 1, wherein the globin is a globin of human origin.

3. The preparation as claimed in claim 1, wherein the homogenized paste can be injected through a hypodermic needle.

4. The preparation as claimed in claim 1, wherein the weight:weight concentration of globin in the injectable preparation is between 30 and 150 mg per gram of preparation.

5. The preparation as claimed in claim 1, wherein the pH of the preparation is between 6 and 8.

6. The preparation as claimed in claim 1, wherein the globin is in suspension.

7. The preparation as claimed in claim 1, further comprising a lubricant.

8. The preparation as claimed in claim 7, wherein this lubricant is selected from the group consisting of solutions of triglycerides, of polyethylene glycol, of hyaluronate, of hyaluronic acid, of oxidized cellulose, and of polysaccharides and of mucopolysaccharides.

9. The preparation as claimed in claim 1, which comprises a crosslinking agent.

10. The preparation as claimed in claim 9, wherein the crosslinking agent is selected from the group consisting of glutaraldehyde, dialdehydes and polyaldehydes, and polysaccharides oxidized with periodic acid, including oxidized dextran, oxidized starch and oxidized hyaluronic acid.

11. The preparation as claimed in claim 1, further comprising at least one of the following active principles: a healing product, a growth factor, and an antibiotic.

12. The preparation as claimed in claim 1, which contains cells, in particular cells cultured using the globin of the preparation as culture support, before injection or implantation, which cells can in particular be skin fibroblasts or chondrocytes.

13. A preparation that can be injected or implanted into the human or animal body, which comprises, as main active component, globin that is insoluble at physiological pH, biocompatible and sterile, wherein the globin is present in the preparation in the form of a gel.

14. The preparation as claimed in claim 13, wherein the globin is a globin of human origin.

15. The preparation as claimed in claim 13, further comprising a lubricant.

16. The preparation as claimed in claim 15, wherein this lubricant is selected from the group consisting of solutions of triglycerides, of polyethylene glycol, of hyaluronate, of hyaluronic acid, of oxidized cellulose, and of polysaccharides and of mucopolysaccharides.

17. The preparation as claim in claim 13, further comprising a crosslinking agent.

18. The preparation as claimed in claim 17, wherein the crosslinking agent is selected from the group consisting of glutaraldehyde, dialdehydes and polyaldehydes, and polysaccharides oxidized with periodic acid, including oxidized dextran, oxidized starchy and oxidized hyaluronic acid.

19. The preparation as claimed in claim 13, which is crosslinked.

20. The preparation as claimed in claim 19, which is crosslinked by the addition of a crosslinking agent and/or by irradiation.

21. The preparation as claimed in claim 13, further comprising at least one of the following active principles: a healing product, a growth factor, and an antibiotic.

22. The preparation as claimed in claim 13, which contains cells, in particular cells cultured using the globin of the preparation as culture support, before injection of implantation, which cells can in particular be skin fibroblasts or chondrocytes.

23. A preparation that can be implemented to the human or animal body, which comprises, as main active component, globin that is insoluble at physiological pH, biocompatible and sterile, wherein said preparation comprises or consists of a globin film, it being possible for the preparation to optionally contain a film-forming agent.

24. The preparation as claimed in claim 23, wherein said film-forming agent is selected from the group consisting of collagen, gelatin, hyaluronic acid, oxidized cellulose, polyethylene glycol and glycerol.

25. The preparation as claimed in claim 23, wherein the globin is a globin of human origin.

26. The preparation as claimed in claim 23, which is crosslinked.

27. The preparation as claimed in claim 26, which is crosslinked by the addition of a crosslinking agent and/or irradiation.

28. The preparation as claimed in claim 27, wherein the crosslinking agent is selected from the group consisting of glutaraldehyde, dialdehydes and polyaldehydes, and polysaccharides oxidized with periodic acid, including oxidized dextran, oxidized starch of oxidized hyaluronic acid.

29. The preparation as claimed in claim 23, further comprising at least one of the following active principles: a healing product, a growth factor, and an antibiotic.

30. The preparation as claimed in claim 23, which contains cells, in particular cells cultured using the globin of the preparation as culture support, before injection or implantation, which cells can in particular be skin fibroblasts or chondrocytes.

31. A preparation that can be injected or implanted to the human or animal body, which comprises, as main component, globin that is insoluble at physiological pH, biocompatible and sterile, wherein said preparation is produced in the form of a solid implant.

32. The preparation as claimed in claim 31, wherein the globin is a globin of human origin.

33. The preparation as claimed in claim 32, which is crosslinked.

34. The preparation in claim 33, which is crosslinked by the addition of a crosslinking agent and/or by irradiation.

35. The preparation as claimed in claim 34, wherein the crosslinking agent is selected from the group consisting of glutaraldehyde, dialdehydes and polyaldehydes, in particular polysaccharides oxidized with periodic acid, including oxidized dextran, oxidized starch and oxidized hyaluronic acid.

36. The preparation as claimed in claim 31, further comprising at least one of the following active principles: a healing product, a growth factor, and an antibiotic.

37. The preparation as claimed in claim 31, which contains cells, in particular cells cultured using the globin of the preparation as culture support, before injection of implantation, which cells can in particular be skin fibroblasts or chondrocytes.

38. A preparation that can be injected or implanted into the human or animal body, which comprises, as main active component, globin that is insoluble at physiological pH biocompatible and sterile, wherein said globin is in suspension in a pharmaceutically acceptable liquid vehicle at a physiological pH and the concentration of globin in the injectable preparation is between 30 and 150 mg per gram of preparation.

39. The preparation as claimed in claim 38, wherein the globin is a globin of human origin.

40. The preparation as claimed in claim 38, wherein the suspension can be injected through a hypodermic needle.

41. The preparation as claimed in claim 38, wherein the pH of the preparation is between 6 and 8.

42. The preparation as claimed in claim 38, further comprising a lubricant.

43. The preparation as claimed in claim 38, further comprising a crosslinking agent.

44. The preparation as claimed in claim 43, wherein the crosslinking agent is selected from the group consisting of glutaraldehyde, dialdehydes and polyaldehydes, in particular polysaccharides oxidized with periodic acid, including oxidized dextran starch and oxidized hyaluronic acid.

45. The preparation as claimed in claim 38, which also contains at least one of the following active principles: healing product, growth factor, antibiotic.

46. The preparation as claimed in claim 38, which contains cells, in particular cells cultured using the globin of preparation as culture support, before injection of implantation, which cells can in particular be skin fibroblasts or chondrocytes.

47. A method for augmenting tissues or filling cavities in a patient in need thereof comprising the step of injecting or implementing in the corporeal location to be augmented or filled, a preparation which comprises, as main active component, globin that is insoluble at physiological pH, biocompatible and sterile.

48. The method according to claim 47, wherein said preparation is in the form of a paste or a gel.

49. The method according to claim 47, wherein said injecting or implanting is for treating skin cavities, wrinkles, defects or scars.

50. A method according to claim 47, wherein said injecting or implanting is for treating connective tissues, sphincters or vocal chords.

51. A method for facilitating healing of cutaneous or internal wounds in a patient in need thereof, comprising the step of injecting or implementing on said wounds, a preparation which comprises, as main active component, globin that is insoluble at physiological pH, biocompatible and sterile.

52. The method according to claim 51, wherein said preparation is in the form of a paste, a gel or a film.

53. A method for facilitating healing of cartilage or bone tissue, in a patient in need thereof, comprising the step of injecting or implanting on said tissues a preparation which comprises, as main active component, globin that is insoluble at physiological pH, biocompatible and sterile.

54. A method for accelerating cell colonization in a corporeal part of a patient in need thereof, comprising the step of injecting or implanting, on said corporeal part, a preparation which comprises, as main active component, globin that is insoluble at physiological pH, biocompatible and sterile.

55. A method for cultivating cells comprising the step of cultivating said cells in the presence of a preparation which comprises, as main component, globin that is insoluble at physiological pH, biocompatible and sterile.

56. The preparation as claimed in claim 23, wherein the film has been obtained by dehydration of a gel or of a solution.

* * * * *